United States Patent [19]
Taylor et al.

[11] Patent Number: 5,588,812
[45] Date of Patent: Dec. 31, 1996

[54] IMPLANTABLE ELECTRIC AXIAL-FLOW BLOOD PUMP

[75] Inventors: Lynn P. Taylor, Camino; Pieter W. J. C. le Blanc, Pollock Pines; Kenneth C. Butler, Carmichael; Timothy R. Maher, Orangevale, all of Calif.

[73] Assignee: Nimbus, Inc., Rancho Cordova, Calif.

[21] Appl. No.: 424,165

[22] Filed: Apr. 19, 1995

[51] Int. Cl.$^6$ .................................................. F04B 17/03
[52] U.S. Cl. .......................... 417/356; 415/900; 604/151
[58] Field of Search ..................................... 417/355, 356, 417/365, 423.1, 423.12, 423.15; 415/900; 604/151; 600/16; 623/3

[56] References Cited

U.S. PATENT DOCUMENTS

| | | | |
|---|---|---|---|
| 3,433,163 | 3/1969 | Sheets et al. | 417/356 |
| 4,625,712 | 12/1986 | Wampler | 128/1 D |
| 4,704,712 | 11/1987 | Moise | 623/3 |
| 4,994,078 | 2/1991 | Jarvik | 623/3 |
| 5,112,200 | 5/1992 | Isaacson et al. | 415/900 |
| 5,158,440 | 10/1992 | Cooper et al. | 417/355 |
| 5,211,546 | 5/1993 | Isaacson et al. | 415/900 |
| 5,399,074 | 3/1995 | Nose et al. | 417/423.12 |

*Primary Examiner*—Timothy S. Thorpe
*Assistant Examiner*—Peter G. Korytnyk
*Attorney, Agent, or Firm*—Harry G. Weissenberger

[57] ABSTRACT

An implantable electric blood pump has a motor stator defining a cylindrical blood conduit, and a pump rotor in which the motor rotor is embedded. The pump rotor is conical at each of its ends and terminates at each end in a ball-and-cup structure washed directly by the pumped blood stream. Grooves may be formed in the ball-and-cup structure to enhance the heat-removing washing action of the blood stream. The pump rotor is nested in the stator blades to shorten the pump and wash the outlet bearing with a partially circumferential blood flow. Titanium-titanium carbide facing alumina are the preferred materials for the rotary-stationary interface, and the gap of the rotary-stationary interface is kept so small that no significant amount of blood serum can penetrate between the mating surfaces of the interface.

17 Claims, 6 Drawing Sheets

IMPLANTABLE ELECTRIC AXIAL-FLOW BLOOD PUMP

FIELD OF THE INVENTION

This invention relates to implantable axial-flow blood pumps using blood-immersed rotors with a non-thrombogenic suspension, and more particularly to a pump configuration using a misalignment-tolerant ball-and-cup rotor support which does not use blood as a bearing fluid.

BACKGROUND OF THE INVENTION

Conventional axial-flow blood pumps with hydrodynamic bearings used in cardiac assist, such as the pump disclosed in U.S. Pat. No. 4,525,712, required a supply of purge fluid to prevent blood from entering their hydrodynamic journal and thrust bearings and causing thrombus formation, hemolysis and bearing seizure. Because of this need for an external fluid supply, that type of pump is not well suited for long-term implants.

Ideally, implantable blood pumps should require no bearing fluid or else use the pumped blood itself, or components of the pumped blood, as a bearing fluid. Indeed, constructions which allow this have been proposed, among others, by R. K. Jarvik in U.S. Pat. No. 4,994,078 and by Isaacson et al. in U.S. Pat. No. 5,112,200. The problem with these constructions is that they rely on cylindrical radial or journal bearings which mechanically support the rotor against radial movement. In typical embodiments of the prior art, those bearings are interior film bearings, i.e. blood-lubricated cylindrical hydrodynamic bearings through which blood serum is drawn by the pressure differential between the ends of the cylinder. In order to prevent blood cells from entering the bearing and being hemolyized, the bearing clearance is made so small that blood cells are essentially precluded from entering the bearing.

Alternatively, as taught by U.S. Pat. No. 4,704,121 to Moise, bearing fluid for a magnetically driven blood pump can be obtained by filtering a portion of the pumped blood through a filter which retains the blood cells and proteins but passes the serum.

Papers entitled "Axial Flow Ventricular Assist Device: System Performance Considerations" (*Artificial Organs*, Vol. 18, No. 1 pp., 44–48 (1994) and "An Ultimate, Compact, Seal-less Centrifugal Ventricular Assist Device: Baylor C-Gyro Pump" (*Artificial Organs*, Vol. 18, No. 1, pp. 17–24 (1994) describe, respectively, an axial-flow blood pump and a centrifugal blood pump using blood-lubricated pivot bearings.

The journal or radial bearing concepts of the prior art have a potential flaw which puts them at risk to bearing seizure, and/or ultimately causes them to undergo excessive bearing material wear. Fundamentally, this is due to the length of the bearing, the diminished heat removal capacity caused by the location of the bearings inside the rotor or stator, and to the lack of significant bearing through-flow in the interior film designs. The comparatively long and extremely narrow gaps the blood must pass through are subject to be plugged by denatured blood products. This is particularly true in those prior art embodiments in which the journal bearing is closed at one end, so that blood cannot flow through it. Even in those designs in which the motor has sufficient torque to machine through any residue formed, significant material wear can occur over the long term and reduce the pump's useful life. Also, in journal bearings using the extremely small tolerances necessary to prevent entry of blood cells, the slightest misalignment of the rotor with respect to the stator can seriously impair the functioning and the life of the pump. Finally, the performance and longevity of journal bearings, including interior film blood bearings, are significantly more dependent on difficult-to-control patient variables such as blood chemistry and hemorrhology than arrangements which do not use blood lubrication.

A need therefore exists for an implantable blood pump in which blood lubrication is unnecessary, alignment is not critical, the interface area between rotating and stationary elements is kept very small, and the interface has superior heat-removing ability and resists any shape changes due to wear.

SUMMARY OF THE INVENTION

In its preferred embodiment, the blood pump of this invention fills the above-identified need by suspending the pump rotor in a ball-and-cup support that has very small mating surfaces with no significant gap between them. The ball-and-cup support does not require the introduction of a lubricating blood serum film between the mating surfaces. The support is washed externally by the pumped blood stream to remove the frictional heat generated at the rotary-stationary interface. Wear is minimized, and heat is efficiently dissipated in accordance with one aspect of the invention, by fabricating the rotary-stationary interface from a titanium-titanium carbide (Ti—TiC) element running against an alumina element. Ti—TiC is preferred for this application because it has high temperature conductivity and therefore runs cooler when washed by the blood stream. In addition, any wear that occurs in spite of the hardness of the ball and cup materials is compensated by so shaping the balls and cups that the shapes of the hemispherical surfaces with respect to each other are not changed by wear, and by optionally maintaining a preload regardless of wear with the aid of a resilient insert in the rotor shaft.

In accordance with another aspect of the invention, the pump rotor is formed with a tail cone which is nested inside the stator blades at the outlet end of the pump. This construction has the double advantage of substantially shortening the overall length of the pump, and of washing the outlet and ball-and-cup structure with a blood stream that still has a substantial circumferential velocity component for improved heat removal action.

In a third aspect of the invention, the balls or cups of the ball- and-cup structure may be equipped with longitudinal grooves which enhance the heat removal action.

DESCRIPTION OF THE PREFERRED EMBODIMENTS

Figure 1:
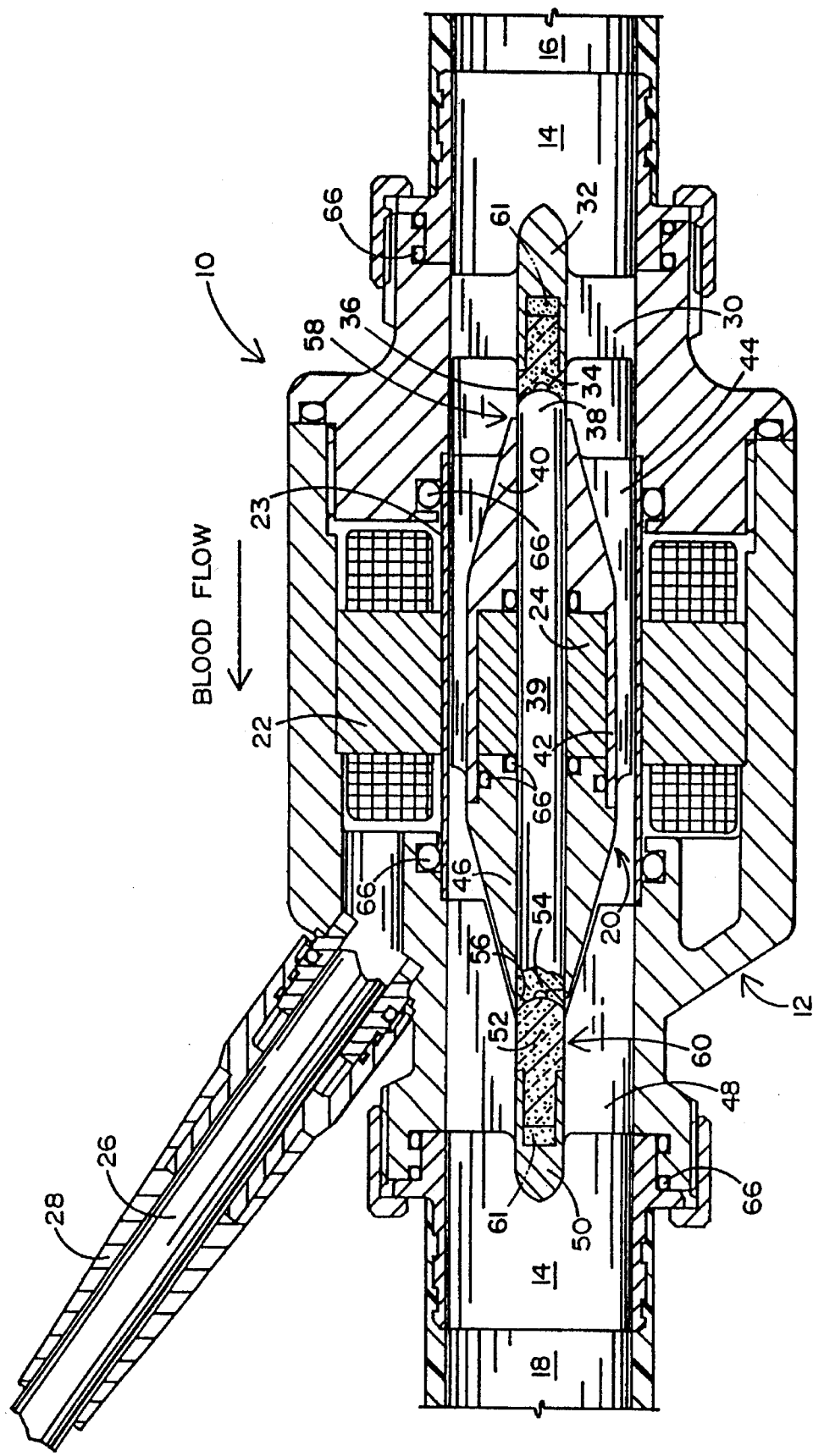
FIG. 1 is a longitudinal section of one embodiment of the pump of this invention.
Figure 2:
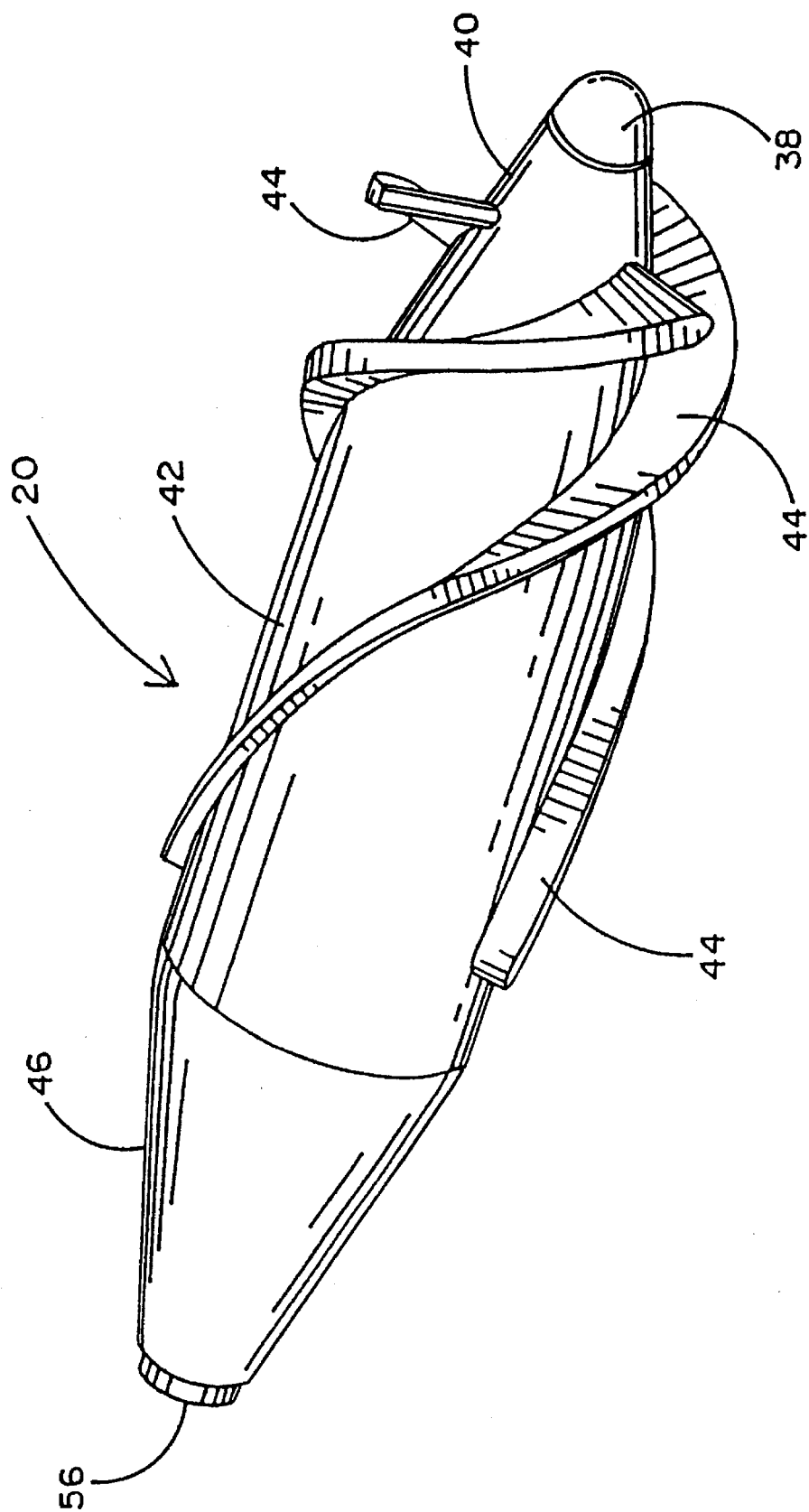
FIG. 2 is a perspective view of the pump rotor of the pump of FIG. 1.

FIG. 1 shows an axial cross section of one embodiment of the inventive pump 10. The pump housing 12 defines a cylindrical blood conduit 14 through which blood is pumped from the inlet 16 to the outlet 18 by the pump rotor 20 best shown in FIG. 2. Motive power for the pump rotor 20 is provided by the interaction of a motor stator 22 surrounding the stator tube 23 in the housing 12, and a motor rotor 24 fixedly mounted in the pump rotor 20. Electrical power is supplied to the motor stator 22 by a cable 26 extending through the wiring conduit 28.

Inside the blood conduit 14, straight inlet stator blades 30 support an inlet hub 32 which contains the cup 34. Grooves 36 (best shown in FIG. 3) may optionally be cut at several circumferential locations in cup 34 to expose to the blood flow more surface area of the rotary/stationary interface formed by the cup 34 and the ball 38 which extends from the nose cone 40 of the pump rotor 20 at the inlet end of pump rotor shaft 39. Whether or not the grooves 36 are used, the opposing interface surfaces in the inventive pump form very short passages, and both the ball 38 and the cup 34 are exposed directly to the main blood flow for efficient heat removal.

The nose cone 40 and the body 42 of pump rotor 20 support the rotor blades 44 which accelerate the blood flowing through blood conduit 14 and impart a circumferential spin to the blood flow. In accordance with this invention, the tail cone 46 of pump rotor 20 is nested within the outlet stator blades 48. The outlet stator blades 48 slow and de-spin the blood flow for discharge into the outlet 18. The outlet stator blades 48 also support the outlet hub 50 which contains the outlet ball 52. The ball 52 cooperates with an outlet cup 54 formed on the outlet end of pump rotor shaft 39 where it protrudes from the tail cone 46.

Figure 5:
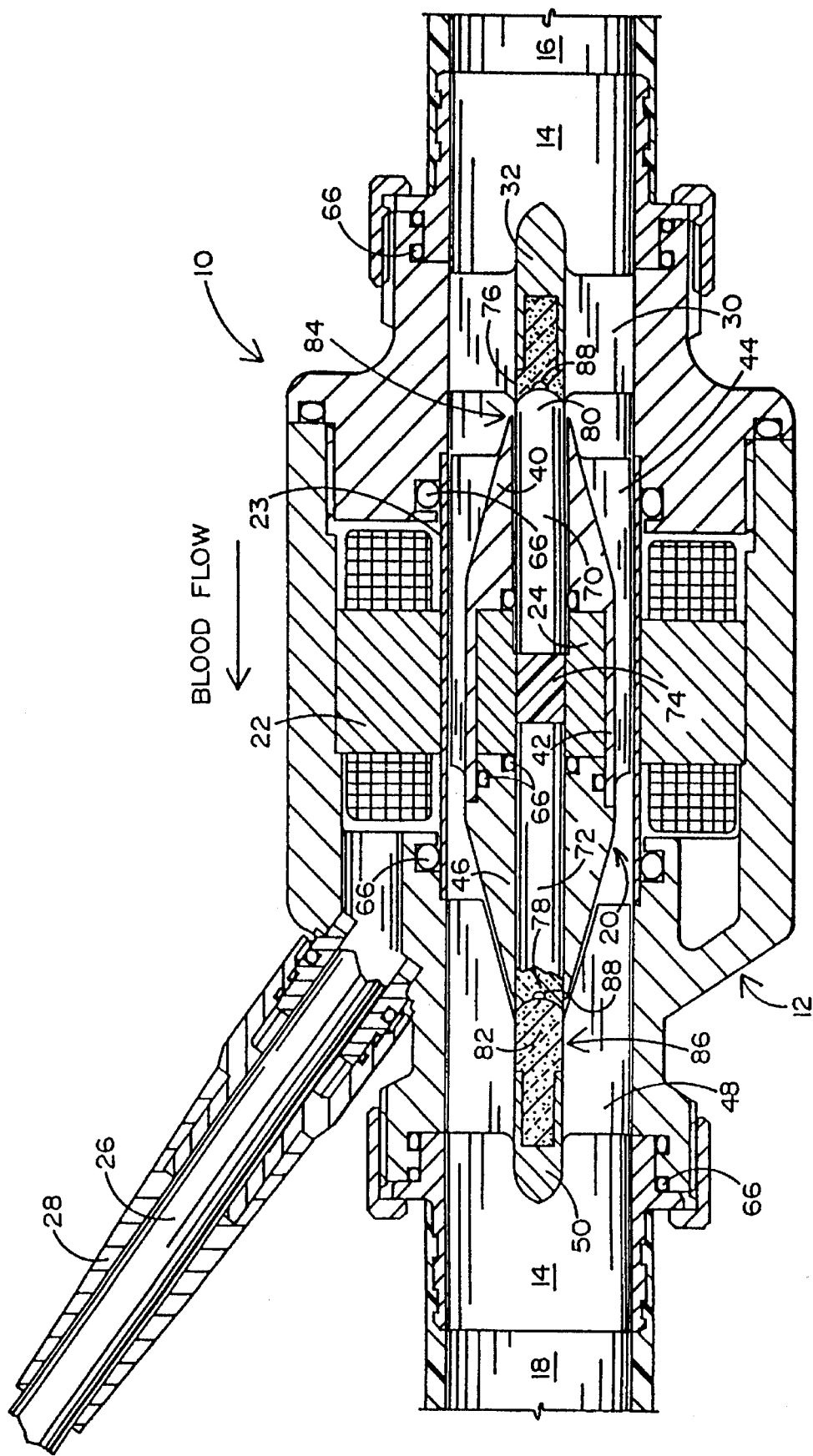
FIG. 5 is a longitudinal section of another embodiment of the pump of the invention.
Figure 6:
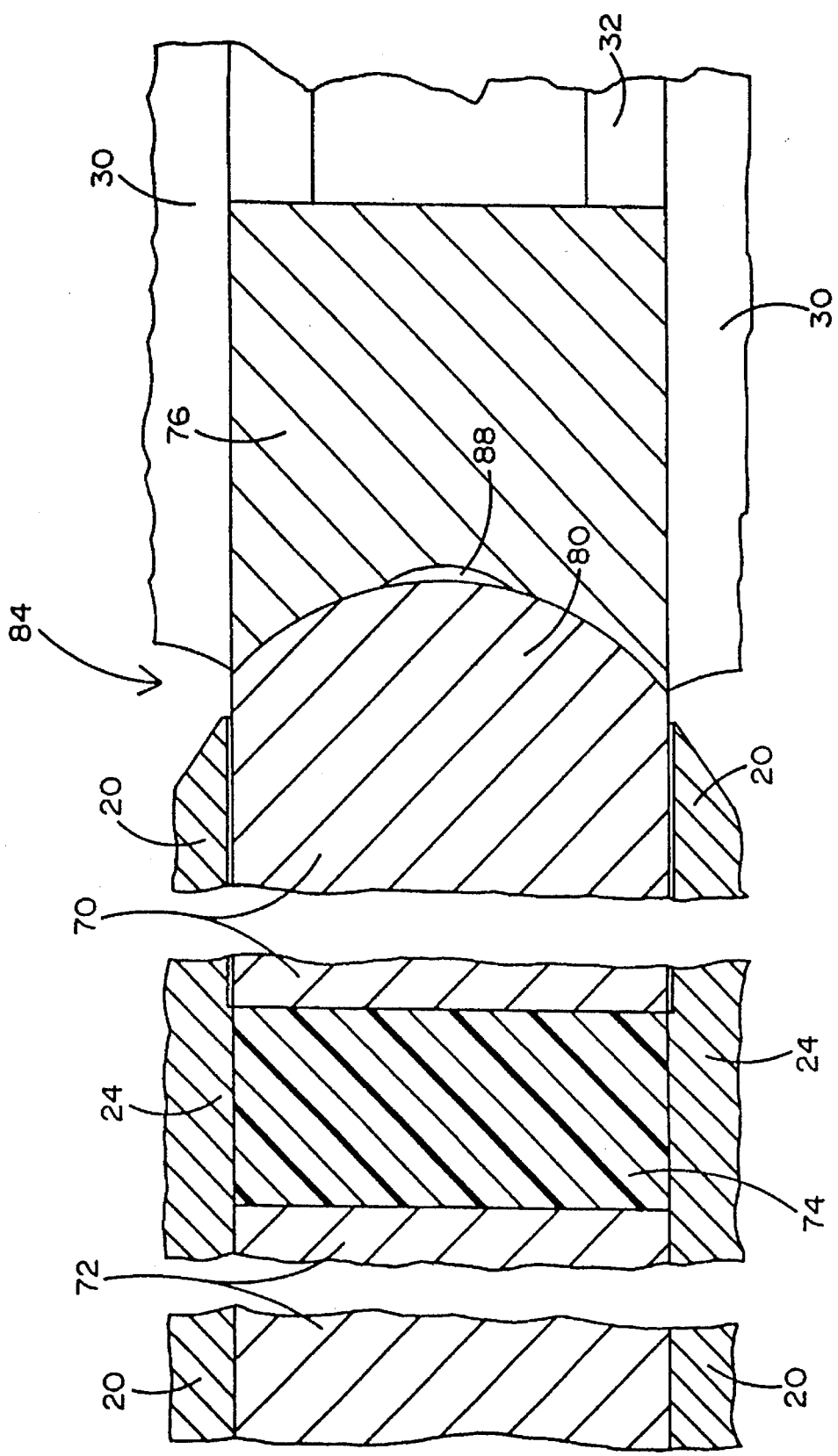
FIG. 6 is a detailed partial section of the rotor and stator of the pump of FIG. 5.

In accordance with a preferred embodiment of the invention illustrated in FIGS. 5 and 6, the pump rotor 20 is provided with a shaft assembly composed of a fixed shaft portion 72, a shaft portion 70 which is axially slidable within the rotor 20 but non-rotatable with respect thereto, and a resilient plug 74 between them. The shaft portion 70 is fitted into rotor 20 with a small enough tolerance (e.g. 50µ) to prevent any blood or serum entering the rotor 20, although it would not matter if it did, because shaft portion 70 does not rotate with respect to rotor 20.

In accordance with the invention, the balls 80, 82 and the respective cups 76, 78 are lapped together during manufacture so that the radii of their hemispherical mating surfaces are as identical as manufacturing techniques can make them. As a result, the gap between the mating surfaces of the balls and their respective cups is extremely small—on the order of 0.25–0.5µ—when the balls and cups are biased against each other by the plug 74.

When the pump of this invention is new, a microscopic amount of manufacturing lubricant fills this extremely narrow gap. A small amount of blood serum may penetrate into the gap, but any serum leakage does not affect the interaction of the mating surfaces.

The hemispherical surfaces of the balls 80, 82 and the cups 76, 78 are preferably less than half hemispheres; for example, the radius of the ball or cup may be about 2 mm, and the diameter of the shaft portion 70 or 72 may be about 3 mm. This improves the sturdiness of the cup rim and results in more uniform wear. A recess 88 may be formed in the center of the cup 76 or 78 for fabrication reasons.

It will be apparent from an examination of FIG. 6 that a slight angular misalignment of the axes of the ball and the cup will not affect the operation of the ball-and-cup structure, as the mating surface of the ball and cup mate in exactly the same way regardless of any slight axial angle alignment variation.

During assembly, the shaft portions 70, 72 are pressed together with sufficient force to deform the resilient plug 74. As the cups 76, 78 wear or the balls and cups expand due to frictional heat, the plug 74 expands and contracts as necessary to maintain an even pressure of the balls 80, 82 against the cups 76, 78. Optionally, preloading may be achieved, if desired, by spring-loading cup 34 and ball 52 with springs 61 (shown in dotted lines in FIG. 1) so that cup 34 and ball 52 can follow any longitudinal movement of pump rotor 20. In order to give the ball-and-cup structures a sufficient useful life (up to five years' reliability is expected of long-term implants of this type) in spite of the small interface surface, the rotor shaft 39 of FIG. 1 or the shaft portion 70 in the embodiment of FIG. 5 are made of alumina, while the ball 52 and the cup 34 of FIG. 1 are made of Ti—TiC. In FIG. 5, the shaft portion 72 is preferably made of Ti—TiC, while the cup 78 is made of alumina. It will be understood that although these materials are preferred, other materials that are hard, wear-resistant, machinable and biocompatible, and which have a relatively high thermal conductivity, can be substituted therefor. These very hard substances make it possible to reduce the already low wear of the inventive ball-and-cup structures to a point where the longevity requirement can be met or exceeded, and the superior thermal conductivity of Ti—TiC prevents heat build-up which might promote thrombus formation.

The advantage of the inventive ball-and-socket structure is that the structures 58, 60 and 84, 86 are highly washed and efficiently cooled external bearings, i.e. bearings in which no blood flows into or through any channel located inside the pump rotor or stator. The bearing surface is very small; there is no unidirectional blood flow through the bearing and therefore no accumulation of blood cells (which may be too large to pass through the bearings) around the bearing interface, nor any thrombus formation at the interface; and the perimeter of the bearing surface is continuously washed by the main blood stream. In addition, the outlet ball-and-cup structure 60 or 86 is very efficiently washed because at the location of that structure less than half way along the stator blades 48, the blood stream still has considerable circumferential velocity.

Figure 3:
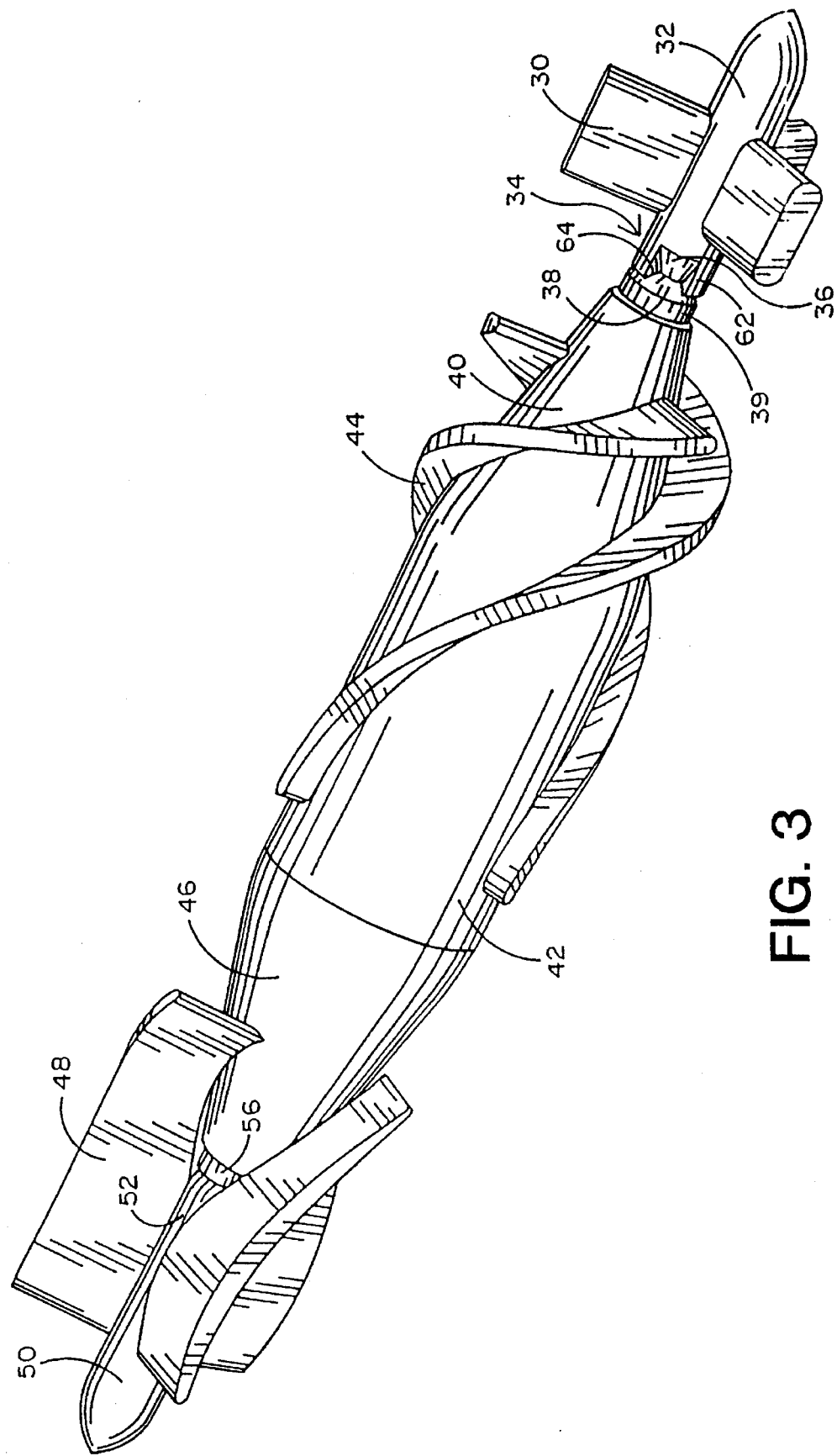
FIG. 3 is a perspective view of the pump rotor and stator assemblies of FIG. 1 with the housing and motor stator removed.
Figure 4:
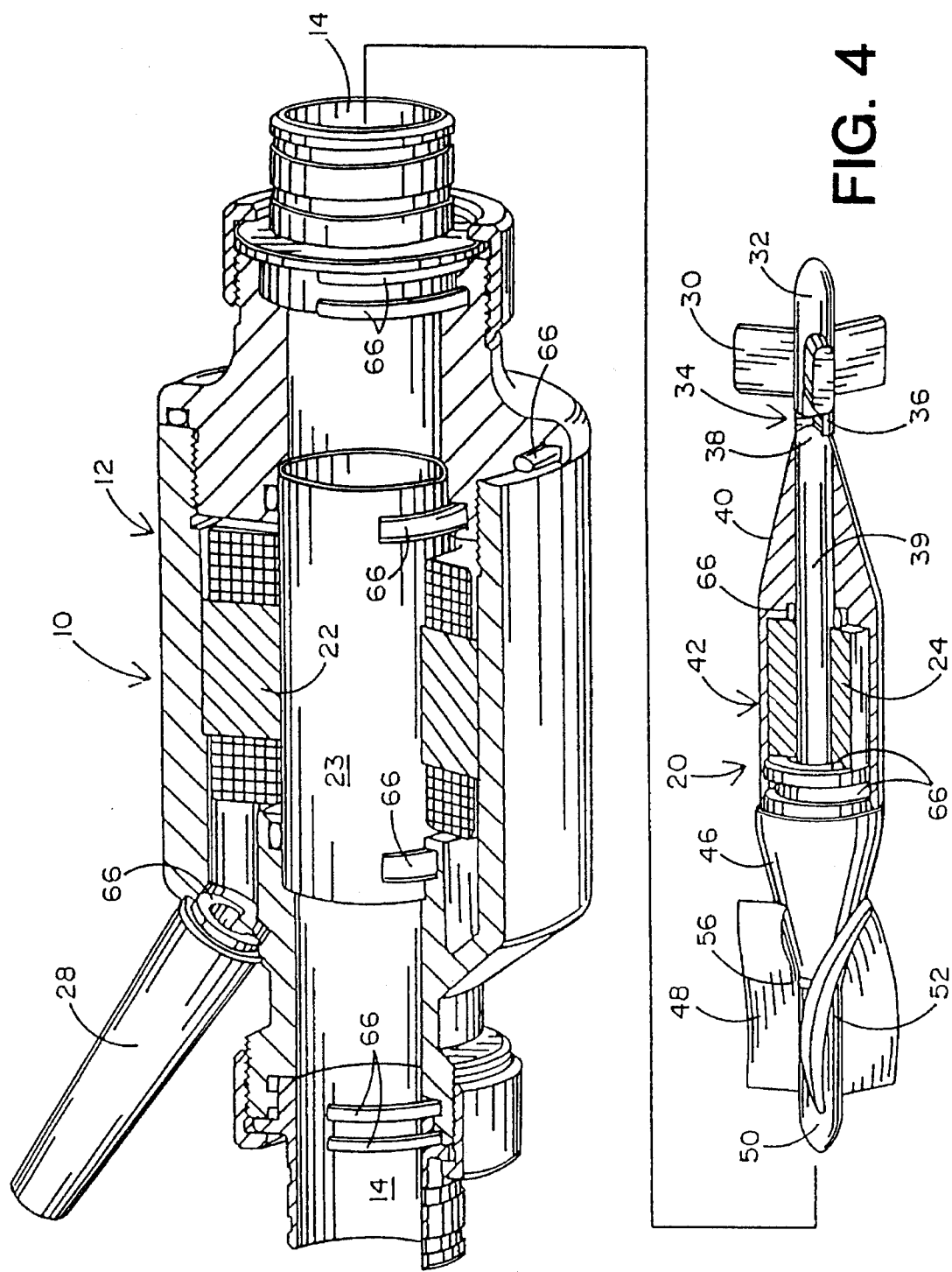
FIG. 4 is a cutaway exploded view of the pump of FIG. 1.

The washing action of the blood stream can be significantly enhanced, if desired, by providing the grooves 36 of FIG. 3. While the portions 62 of cup 34 lying between the grooves 36 in FIG. 1 support the ball 38 against radial or longitudinal movement, blood flowing through the grooves 36 continuously flushes the ball surface. Likewise, in the embodiment of FIGS. 5 and 6, grooves (not shown) may be formed on the balls 80, 82 to enhance the cooling effect of the washing action of the blood stream. All parts of the pump not intended to be washed by the blood stream are sealed off from it by 0-rings generally shown as 66.

We claim:

1. An implantable blood pump comprising:
   a) a cylindrical blood conduit;
   b) a motor stator surrounding said blood conduit;
   c) a pump rotor having inlet and outlet ends and containing a motor rotor for motive interaction with said motor stator, said pump rotor being arranged to rotate in said blood conduit;
   d) inlet stator blades disposed in said blood conduit, said inlet stator blades supporting an inlet hub;

e) outlet stator blades disposed in said blood conduit, said outlet stator blades supporting an outlet hub; and f) a ball-and-cup structure interposed between each of said inlet and outlet ends of said pump rotor and the corresponding one of said hubs for supporting said rotor, said ball-and-cup structures being washed by the blood flow through said blood conduit;

g) said ball-and-cup structure having a substantially smaller diameter than said, pump rotor and presenting to said blood flow a substantially continuous surface through which substantially no blood can penetrate between said ball and cup.

2. The blood pump of claim 1, in which said pump rotor has a cylindrical body portion, a nose portion at said inlet end and a tail cone at said outlet end, said tail cone being nested within said outlet stator blades.

3. The blood pump of claim 2, in which said nesting is such that said ball-and-cup structure at the outlet end of said pump rotor is substantially centered with respect to the longitudinal extent of said outlet stator blades.

4. The blood pump of claim 2, in which said nose portion of said pump rotor carries at its inlet end the ball of said inlet end ball-and-cup structure.

5. The blood pump of claim 4, in which at least one element of said inlet end ball-and-cup structure has longitudinal grooves formed therein, said grooves being exposed to the main blood flow through said pump.

6. The blood pump of claim 2, in which said motor rotor is fixedly disposed in said central portion of said pump rotor, and portions of said ball-and-cup structures are resiliently movable in a direction axial of said pump rotor.

7. The blood pump of claim 2, in which said nose portion is substantially conical.

8. The blood pump of claim 1, in which said inlet and outlet hubs are axially fixed with respect to said motor stator, said motor rotor having a shaft including a pair of shaft portions axially movable with respect to each other but non-rotatable with respect to said rotor, and a resilient element interposed between said shaft portions and arranged to bias said shaft portions axially away from each other.

9. The blood pump of claim 8, in which said resilient element is a plug.

10. The blood pump of claim 8, in which one of said shaft portions is axially fixed with respect to said rotor, and the other shaft portion is axially slidable with respect to said rotor.

11. The blood pump of claim 10, in which said slidable shaft portion is on the inlet side of said rotor.

12. The blood pump of claim 11, in which said slidable shaft portion has a ball on its inlet end and is made of alumina, and said fixed shaft portion has a cup on its end and is made of titanium-titanium carbide.

13. The blood pump of claim 8, in which said ball-and-cup structures are composed of an element constructed of titanium-titanium carbide facing an element constructed of alumina.

14. The blood pump of claim 13, in which said pump rotor has a longitudinal shaft, each end of which is an element of one of said ball-and-cup structures, said shaft being said element constructed of alumina.

15. The blood pump of claim 1, in which said ball-and-cup structures are composed of hard wear-resistant, machinable, biocompatible materials which have a high thermal conductivity.

16. The blood pump of claim 1, in which the mating surfaces of the balls and cups of said ball-and-cup structures are of essentially identical radius.

17. The blood pump of claim 16, in which said balls and cups are biased against one another with sufficient force to substantially prevent penetration of blood between said mating surfaces.

* * * * *